United States Patent [19]
Golub et al.

[11] Patent Number: 5,514,133
[45] Date of Patent: May 7, 1996

[54] ACCESS DEVICE FOR ENDOSCOPIC SURGERY

[76] Inventors: Robert Golub, 36 Clubhouse La., Scarsdale, N.Y. 10583; H. David Stein, 91 Larchmont Ave., Larchmont, N.Y. 10538; Roberto Cantu, Jr., 6 Vanderbilt Dr., Lake Success, N.Y. 11020

[21] Appl. No.: 296,942

[22] Filed: Aug. 26, 1994

[51] Int. Cl.$^6$ ................................................ A61B 17/04
[52] U.S. Cl. ........................ 606/1; 604/175; 604/256
[58] Field of Search ............... 606/1, 2, 3; 604/174, 604/175, 167, 178, 177, 256, 337, 338

[56] References Cited

U.S. PATENT DOCUMENTS

| | | | |
|---|---|---|---|
| 4,069,826 | 1/1978 | Sessions et al. | 604/173 |
| 4,217,664 | 8/1980 | Faso . | |
| 4,338,937 | 7/1982 | Lerman | 604/175 |
| 4,781,176 | 11/1988 | Ravo . | |
| 4,969,902 | 11/1990 | Ravo . | |
| 5,098,393 | 3/1992 | Amplatz et al. . | |
| 5,098,397 | 3/1992 | Svensson et al. | 604/174 |
| 5,108,430 | 4/1992 | Ravo . | |
| 5,176,687 | 1/1993 | Hasson et al. | 606/114 |
| 5,207,685 | 5/1993 | Cinberg et al. | 606/1 X |
| 5,209,736 | 5/1993 | Stephens et al. . | |
| 5,209,754 | 5/1993 | Ahluwalia . | |
| 5,211,633 | 5/1993 | Stouder, Jr. | 604/167 |
| 5,217,441 | 6/1993 | Shichman . | |
| 5,242,409 | 9/1993 | Buelna . | |
| 5,279,575 | 1/1994 | Sugarbaker | 606/1 X |
| 5,300,036 | 4/1994 | Mueller et al. . | |
| 5,366,478 | 11/1994 | Brinkerhoff et al. | 606/213 |

*Primary Examiner*—Stephen C. Pellegrino
*Assistant Examiner*—Michael Peffley
*Attorney, Agent, or Firm*—Pennie & Edmonds

[57] ABSTRACT

An endoscopic surgical apparatus is provided for enabling the surgeon to access directly the surgical site during an endoscopic procedure. The apparatus includes an opening extending longitudinally through the apparatus and being configured and dimensioned to receive a hand therethrough. A first plate engages against the outer surface of the abdominal wall. A second plate is spaced from the first plate and is movable between a first position and a second position wherein the second plate is in close cooperative alignment with the inner surface of the abdominal wall. An adjustment member is mounted to the second plate and actuates movement of the second plate between its first position and its second position. A first sealing member inhibits the flow of gas through said opening and is formed by a pair of overlapping seals. A flexible sleeve extends between the first and second plates and adjusts in length to accommodate various thicknesses of the abdominal wall. The sleeve also creates an access port for the passage of objects through the abdominal wall.

16 Claims, 2 Drawing Sheets

ACCESS DEVICE FOR ENDOSCOPIC SURGERY

BACKGROUND OF THE INVENTION

1. Field of the Invention

This invention relates to an access device for use during endoscopic surgical procedures, and more particularly to an access device which permits a surgeon to insert his hand or a non-endoscopic surgical instrument into the body cavity during an endoscopic surgical procedure.

2. Description of the Related Art

In endoscopic procedures, surgery is performed through small incisions, usually between 5 to 15 mm, in the patient's body. The incisions provide access for a trocar or cannula device which enables the insertion of various surgical instruments into the body cavity. Specialized surgical instruments are then inserted through the trocar or cannula and entire surgical procedures, such as cholecystectomies, hysterectomies and hernia repairs, can be performed through several small incisions. The endoscopic surgical procedures dramatically reduce the pain, discomfort, period for recuperation and blood loss which result from the large incision necessary to perform a traditional open procedure. Examples of endoscopic procedures and the instruments used for such a procedure are disclosed in U.S. Pat. Nos. 5,190,561 and 5,271,385, the contents of which are incorporated herein by reference.

For an endoscopic surgical procedure to be performed in the abdominal cavity, the abdominal wall must be elevated from the organs in the intra-abdominal cavity. This is usually accomplished by inserting a Verres needle into the intra-abdominal cavity and initiating insufflation to the desired intra-abdominal pressure. In order for endoscopic procedures in the intra-abdominal cavity to be performed the insufflation must be maintained, as the abdominal wall must remain elevated from the organs in the intra-abdominal cavity. The preferred or necessary level of insufflation is often difficult to maintain because as each endoscopic surgical instrument is inserted into and removed through the trocar or cannula, insufflation gas is allowed to escape from the intra-abdominal cavity. This escape of insufflation gas and the potentially resultant surgical situation is undesirable.

While endoscopic procedures have met with tremendous acceptance, to the extent that the vast majority of cholecystectomies are performed endoscopically, the adaptation of endoscopic surgical procedures into other surgical procedures has been limited by the present need for all instruments used during an endoscopic procedure be sized to fit through the trocar or cannula device. The adaptation of other surgical procedures has further been hampered by the requirement that all objects removed from the surgical site be sized to fit through the trocar or cannula. The special endoscopic surgical instruments are different from the traditional surgical instruments which surgeons have been using for decades and have the further undesirable drawback of reduced tactility. An additional constraint imposed on the present endoscopic hand instrument is that they are quite expensive to manufacture and only a representative few instruments are available. Also, one additional drawback to endoscopic surgery is the inability of the surgeon to have his hand directly at the surgical site. The ability of the surgeon to perform some surgical techniques, such as suturing, and to touch, feel and manipulate directly at the surgical site further hinders the adaptation of endoscopic surgery to additional surgical procedures.

Numerous devices for facilitating introduction into a body cavity have heretofore been proposed in relation to various types of surgical devices and instruments. For example, U.S. Pat. No. 5,242,409 discloses an access device for accommodating the introduction of an instrument with a bent configuration and having a cannula and a hub disposed at the proximal end thereof. U.S. Pat. No. 5,217,441 discloses a guide tube positioning device for positioning a guide tube relative to the body once the desired penetration has been obtained. U.S. Pat. No. 5,300,036 discloses a trocar having multiple converters for adopting the size of the annular seal located on the trocar tube to different sizes of instruments. This allows the same trocar body subassembly and trocar tube subassembly to be used for various sizes of surgical tools. U.S. Pat. No. 5,209,736 discloses a trocar assembly having trocar tubes of different diameters to accommodate various diameters of instruments. The lumen of the outer trocar tube and, therefore, the largest instrument which could be passed therethrough is approximately 50 mm.

The devices discussed above were all designed to be used in endoscopic surgical procedures and all require that instruments inserted through them be appropriately configured and dimensioned and have a diameter not larger than approximately 50 mm.

There is a need for an access device and method of utilizing such devices that permits the insertion of a surgeon or nurse's hand and other large diameter instruments through the abdominal wall to the surgical site while also maintaining insufflation. Such a device would increase the kinds of surgical procedures that could be performed endoscopically by allowing a surgeon to advance his hand to the surgical site as well as to use traditional open procedure surgical instruments. Also, such a device would permit the removal of tumors or other relatively large body parts from the body through an opening in the abdominal wall.

Because endoscopic procedures are more common than laparoscopic procedures, the present invention shall be discussed in terms of endoscopic procedures and apparatus. However, use herein of terms such as "endoscopic" and "endoscopically", among others, should not be construed to limit the present invention to an apparatus for use only in conjunction with an endoscopic tube. To the contrary, it is believed the present invention may find use in any procedure where access is limited to a small incision, including but not limited to laparoscopic procedures.

3. Objects of the Invention

Accordingly, it is one object of the present invention to provide an access device for use during endoscopic surgery.

A further object of the invention is to provide an access device for use during endoscopic surgery and which is adapted and configured to receive a surgeon's hand or large instrument therethrough.

Another object of the invention is to provide an access device which maintains insufflation during an endoscopic surgical procedure and also permits the passage of a surgeon's hand or surgical instrument or other similarly sized object through the abdominal wall and into the body cavity.

SUMMARY OF THE INVENTION

In accordance with the present invention, an access device for endoscopic surgery is provided having a first plate, second plate and sleeve positioned therebetween. An opening extends longitudinally through the device and is configured and dimensioned to receive a hand therethrough.

The first plate includes a proximal surface and an abdomen engaging surface for engaging the outer surface of the abdominal wall. The second plate is spaced from said first plate and includes a distal surface and an inner abdominal wall engagement surface. The second plate is movable between a first position wherein the second plate is spaced from the abdominal wall and a second position wherein the second plate is in engagement with the inner surface of the abdominal wall such that the abdominal wall is securely positioned between the first and second plates.

The flexible sleeve includes a plurality of bellows which are expandable and contractible to adjust the length of the sleeve to the first and second positions of the second plate.

A plurality of adjustment members fixedly extend from the second plate through the first plate. The adjustment members actuate movement of the second plate so that, in use, movement of the adjustment members in a proximal direction causes movement of the second plate in a proximal direction and into engagement with the abdominal wall.

A corresponding plurality of anchor members extend from the first plate for cooperating with the adjustment members. The position of the adjustment members, and the second plate attached thereto, is retained by engaging the adjustment members around the anchor members.

A first seal assembly comprising a pair of cooperating seals is also provided in the device. The cooperating seals extend from the first plate and inhibit the escape of insufflation gases. A second seal assembly is mounted on the first plate and additionally inhibits the escape of insufflation gas.

BRIEF DESCRIPTION OF THE DRAWINGS

The access device for endoscopic surgery will be described hereinbelow with respect to the drawings wherein.

DETAILED DESCRIPTION OF THE PREFERRED EMBODIMENTS

Figure 1:
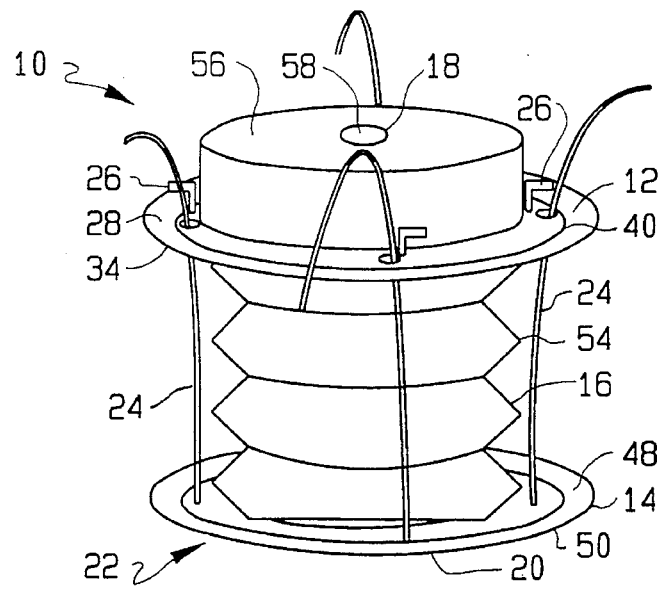
FIG. 1 is a perspective view of an access device for use in endoscopic surgery in accordance with a preferred embodiment of the present invention.

In the drawings and in the description which follows, the term "proximal", as is traditional, will refer to the end of the subject invention which is closest to the operator, while the term "distal" will refer to the end of the apparatus which is furthest from the operator.

Figure 3:
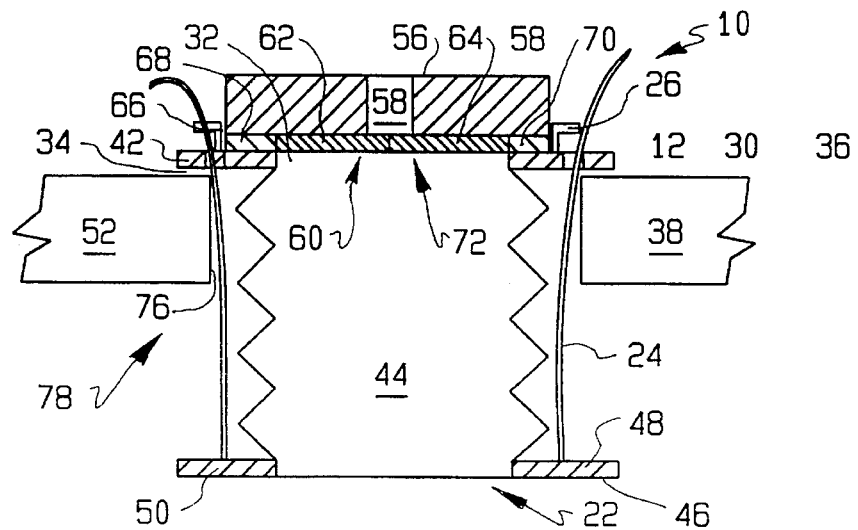
FIG. 3 is a side elevational view of the access device of FIG. 1.

The surgical apparatus of the subject invention is illustrated in FIG. 1 and FIG. 3 and designated generally by reference numeral 10. In a preferred embodiment, the surgical apparatus 10 has a first plate 12 and a second plate 14 spaced therefrom. An elongated flexible sleeve 16 extends between the first and second plates 12, 14, respectively, and is expandable and contractible longitudinally. The apparatus 10 has an open proximal end 18 and an open distal end 20 that define an opening 22 (see FIG. 3). The opening 22 is sized and configured to receive therethrough an object, such as a surgeon's hand or large open-procedure surgical instrument, between approximately 50 mm and 100 mm in diameter, and preferably between 60 mm and 90 mm, although smaller or larger sizes and various shapes may be utilized. A plurality of adjustment 24 members are fixed to and extend proximally from the second plate 14 and through the first plate 12. A corresponding plurality of anchor members 26 are mounted on the first plate 12 to receive and fixedly position the adjustment members 24.

The first plate 12 is a disc-shaped member having a proximal surface 28 and an abdominal wall engaging surface 30 (see FIG. 3). An opening 32 is formed in the first plate 12 to receive a surgeon's hand or large surgical instrument. Preferably, the first plate 12 has a non-slip surface 34, such as for example silastic, to ensure the wall engaging surface 30 securely engages the outer surface 36 of the abdominal wall 38. A reinforced portion 40 of the first plate 12 is formed of a biocompatible hardened material such as ABS plastic or metal and has mounted thereon the anchors 26 and also includes plurality of openings 42 for receiving the adjustment members 24 therethrough.

The second plate 14 is also a disc shaped member having an opening 44 formed therein to receive a surgeon's hand or large surgical instrument therethrough. The second plate 14 includes a distal surface 46 and a proximal abdominal wall engaging surface 48 which is preferably treated with a non-slip agent 50, such as for example silastic, to ensure secure engagement between surface 48 of the second plate 14 and the abdominal wall inner surface 52. Alternatively, either or both of wall engaging surfaces 30 and 48 may be provided with small teeth or other projections in order to further increase the non-slip characteristic.

The sleeve 16 extends between the first and second plates 12, 14 and includes a plurality of bellows 54 for facilitating the longitudinal expansion and contraction of the sleeve member 16. While the sleeve 16, first plate 12 and second plate 14 have all been described separately, it will be appreciated by those skilled in the art that the sleeve 16, first plate 12 and second plate 14 could be formed of an integral, one piece construction. Preferably, sleeve 16 and first and second plates 12, 14 are made of a plastic material, such as polyurethane or polypropylene.

The position of the second plate 14 is adjusted by the adjustment members 24 which are fixedly attached, for example by an adhesive or by a manufacturing process such as insert molding, to second plate 14. In a preferred embodiment, the adjustment members 24 are sutures, although it will be appreciated by those in the art that any elongated, flexible strong element, such as plastic strips or wires could be used for the same adjustment purposes.

A proximal seal member 56 having an opening 58 through which a surgeon's or assistant's hand may be inserted is mounted to the first plate 12. The proximal seal 56 inhibits the escape of insufflation gases from the abdominal cavity 78 during the surgical procedure. The proximal seal member 56 is formed of a material, such as silastic, foam, or cellular polyethylene, which seals and expands when a hand or instrument is inserted through the opening 58, but which returns to its original shape to seal around the member inserted through the opening or once the object has been removed.

Figure 2:
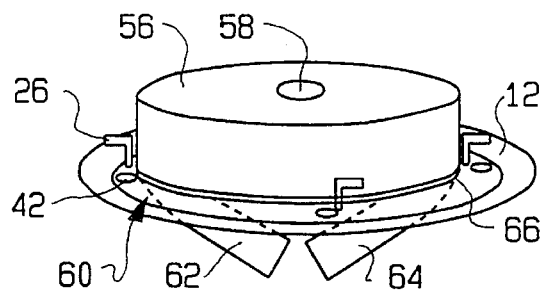
FIG. 2 is a perspective view of the first plate and seal assembly of the access device of FIG. 1 with the flap valve seals shown in an open position.

Referring to FIGS. 2 and 3 there is shown the cooperating seal assembly 60 which is formed by a pair of cooperating flap valve seals 62, 64 mounted in a valve seat member 66. The flap valve seals 62, 64 of known construction are suitably hinged at 68, 70 and are movable between a sealing position 72 in sealing contact with valve seat member 66 (see FIG. 3) and an open position 74 (see FIG. 5) extending distally and pivoted relative to valve seat member 66. The cooperating seal assembly 60 is mounted to the first plate 12 between the proximal seal 18 and sleeve 16. Alternatively, the flap valve seals 62, 64 could be a pair of envelope seals formed of polyurethane or polypropylene. Also, it is contemplated that the flap valve seals could be activated by an actuation member mounted on the outer surface of the seal assembly for actuating opening and closing of the flap valve seals.

Figure 4:
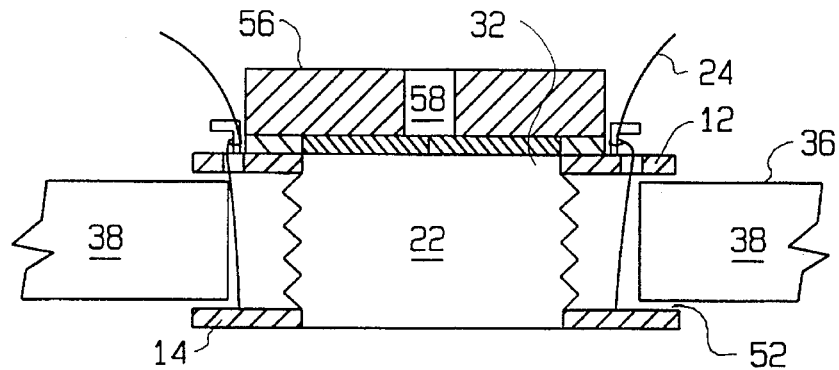
FIG. 4 is a side elevational view of the access device of FIG. 1 illustrating the first and second plates in firm engagement with the abdominal wall.

The unique features of access apparatus 10 will become more apparent from the following description of the operation thereof. An incision 76 is made in the abdominal wall 38 between 50 mm to 100 mm. The incision 76 must be appropriately sized so that the second plate 14 can be inserted through the incision 76, but not so large that the first plate 12 is inserted through the incision 76 into the abdominal cavity 78. The second plate 14 is inserted through the incision 76 to cause the abdominal wall engaging surface 30 of the first plate 12 to firmly mount onto the outer surface of the abdominal wall and the second plate 14 to be positioned distal to the abdominal wall 38 as shown in FIG. 3. The adjustment members 24 are grasped and pulled proximally to cause the first plate 12 to also advance proximally and into engagement with the inner surface 52 of the abdominal wall 38. Once the second plate 14 is in engagement with the abdominal wall 38 and between the second plate 14 and first plate 12 (see FIG. 4), the adjustment members 24 are anchored around the anchor members 26.

Figure 4A:
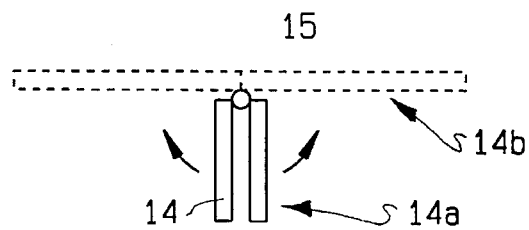
FIG. 4A schematically illustrates an alternative preferred embodiment of the second plate.

In an alternative preferred embodiment, second plate 14 is constructed with a one-way hinge 15 as shown in FIG. 4A. The hinge permits bottom plate 14 to be folded to position 14a, to facilitate introduction through the incision in the abdominal wall. Once through the incision, adjustment members 24 are pulled up to unfold plate 14 in the direction of the arrows to position 14b (shown in dashed lines). Hinge 15 is configured such that the plate does not fold beyond position 14b, so a flat, stiff surface is pulled against the abdominal wall and secured by adjustment members 24. Alternatively, plate 14 may be made of a plastic or composite construction which permits the folding action described above without a separate hinge. Sleeve 16 is sufficiently flexible to permit plate 14 to move to position 14a, but may tend to bias the plate toward position 14b if so desired.

Figure 5:
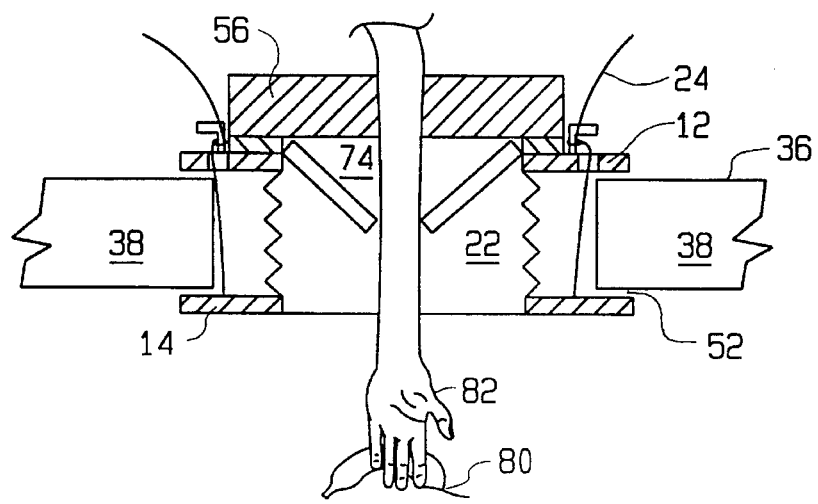
FIG. 5 is a side elevational view of the access device of FIG. 4 with a surgeon's hand inserted therethrough.

As shown in FIG. 5, a surgeon may then insert his hand 82 (or a surgical instrument) through the apparatus 10 for use directly at the surgical site 80. In use, a hand 82 is inserted through the proximal seal 56 which will expand to receive the object, which in FIG. 5 is a hand, inserted therethrough. As the object is advanced further, the cooperating seals 62, 64 pivot for the passage of the hand 82 or surgical instrument. The hand 82 or surgical instrument is then advanced through, first plate 12, sleeve 16, second plate 14 and to the surgical site 80 where the surgeon may then perform a procedure. Also, tools of various sizes, and particularly those used during an open procedure, may be advanced to the surgical site 80.

From the foregoing, it will be observed that numerous modifications and corrections can be effected without departing from the true spirit and scope of the novel concept of the present invention. For example, in the preceding paragraph the discussion of use refers to a surgeon's hand being inserted into the apparatus. It would be understood by those in the art that a surgical instrument could be inserted through the apparatus and advanced to the surgical site and that alternatively a piece of rejected tissue could be removed from the surgical site and through the apparatus. It will be understood that no limitation with respect to the specific embodiments illustrated herein is intended or should be inferred.

We claim:

1. A surgical apparatus comprising:

a first plate having an abdominal wall engaging surface for engaging the outer surface of the abdominal wall;

a second plate cooperating with said first plate and adapted to receive the abdominal wall therebetween, said second plate being movable between a first position distal to the abdominal wall and a second position which engages the inner surface of the abdominal wall such that the abdominal wall is positionable between said first and second plates;

a sleeve having an adjustable length and extending from said first plate for providing access through the abdominal wall, said sleeve and said first and second plates defining an opening extending longitudinally through said apparatus and adapted and configured for receiving a hand therethrough, said sleeve further having a collapsible bellows for facilitating the adjustment in length of the sleeve;

a sealing member for inhibiting the escape of insufflation gas through said opening during a surgical procedure;

an adjustment member fixedly extending from said lower plate to said upper plate such that movement of said adjustment member in a direction toward said first plate correspondingly moves said second plate from said first to said second position; and an anchor for receiving said adjustment member and maintaining the position thereof.

2. A surgical apparatus as recited in claim 1, wherein said sealing member comprises a first seal and a second seal which cooperate such that any insufflation gas which escapes through said first seal is prevented by said second seal from escaping through said opening.

3. A surgical apparatus as recited in claim 1 wherein said opening has a diameter between about 50 mm and 100 mm and extends in length from said upper plate to said lower plate.

4. A surgical apparatus as recited in claim 3 wherein a top surface of said second plate and a bottom surface of said first plate further comprise a non-slip surface between the first and second plates and the abdominal wall positioned therebetween.

5. A device for use during an endoscopic surgical procedure, comprising:

a first plate for engaging the outer surface of the abdominal wall;

a second plate spaced from said first plate and having a surface for engaging the inner surface of the abdominal wall, said second plate is movable between a first position wherein the second plate is spaced from the abdominal wall and a second position wherein said second plate is engaging the inner surface of the abdominal wall;

a sleeve for providing access through the abdominal wall extending between said first and second plates and defining therethrough an opening extending longitudinally from a proximal to a distal end of said device and being sized and configured to receive a hand therethrough, said sleeve further having a collapsible bellows for facilitating the adjustment in length of the sleeve; and an adjustment member extending from said second plate to said first plate for moving said second plate, such that movement of said adjustment member correspondingly moves said second plate from said first to said second positions.

6. A device as claimed in claim 5 further comprising a first seal member which at least partially closes said opening to inhibit the escape of insufflation gas through said opening during a surgical procedure.

7. A device as claimed in claim 6 wherein said first seal member is a pair of cooperating and at least partially overlapping seals extending from said first plate.

8. A device as claimed in claim 5 wherein said adjustment member is fixedly attached to said second plate and moving said adjustment member correspondingly moves said second plate to bring said second plate into close cooperative alignment with said first plate, such that said first and second plates are secured to the abdominal wall.

9. A device as claimed in claim 5 further comprising an anchoring member secured to said first plate for receiving and retaining said adjustment member in a fixed position.

10. A device as claimed in claim 5 further comprising a second seal member extending from said first plate for further inhibiting the escape of insufflation gas through said opening during a surgical procedure by at least partially closing said opening.

11. A device as claimed in claim 10 wherein second plate abdominal wall engaging surface has projections thereon for enhancing engagement with the wall.

12. A surgical access port for providing a substantially gas-tight access opening to an abdominal cavity through the abdominal wall, comprising:

an outer member for positioning outside the abdominal cavity and defining a passageway to the abdominal cavity;

an inner member adapted to be inserted through an incision in the abdominal wall for positioning inside the abdominal cavity, said inner member and outer members defining a passageway to the abdominal cavity, said inner member movable between a first position in which said inner member is adjustable relative to the abdominal wall and a second position wherein said inner member is engaged against the abdominal wall which is secured between the inner and outer members;

a flexible, expansible sleeve extending between the inner and outer members to define a gas-tight passage between the inner and outer member openings, said sleeve movable between a first position which corresponds to said inner member first position and a second position which corresponds to said inner member second position and the engagement of the inner member against the abdominal wall secured between inner and outer members, wherein the flexibility of the sleeve permits the movement between said first and second positions and adjustment of the inner member relative to the outer member and abdominal wall;

a sealing element disposed in said passage, said element adapted to receive, with an at least substantially gas-tight seal, a surgeon's hand passing through said passage, and being adjustable to form at least a substantially gas-tight seal when the surgeons hand is withdrawn and inserted.

13. The access port according to claim 12, further comprising at least one securing member extending between said inner and outer members such that movement of said at least one securing member causes corresponding movement of said inner member to draw together and securing said inner and outer members against the abdominal wall.

14. The access port according to claim 13, wherein said securing member comprises an elongated flexible member mounted to said inner member for positioning said inner member relative to the abdominal wall.

15. The access port according to claim 12, wherein said sealing element comprises a distal, split seal for sealing said passage in the absence of an object inserted therethrough and a proximal expandable annular seal for sealing around the object inserted therethrough.

16. The access port according to claim 12, wherein said inner member includes hinge means for folding the inner member substantially in half in one direction to facilitate insertion through the incision.

* * * * *